United States Patent [19]
Flesher et al.

[11] Patent Number: 6,113,767
[45] Date of Patent: Sep. 5, 2000

[54] ELECTROPHORESIS SEQUENCING APPARATUS

[75] Inventors: Robert W. Flesher, Baltimore; Kevin J. Barnes, Uniontown, both of Md.

[73] Assignee: Apogee Designs, Ltd., Baltimore, Md.

[21] Appl. No.: 09/065,901

[22] Filed: Apr. 24, 1998

[51] Int. Cl.[7] .................... G01N 27/27; G01N 27/403
[52] U.S. Cl. .......................... 204/608; 204/603
[58] Field of Search .................. 204/450, 451, 204/452, 453, 456, 457, 461, 466, 600–606, 608, 612, 616, 617

[56] References Cited

U.S. PATENT DOCUMENTS

| | | |
|---|---|---|
| 3,129,158 | 4/1964 | Raymond et al. . |
| 3,208,929 | 9/1965 | Raymond et al. . |
| 3,290,240 | 12/1966 | Neren . |
| 3,867,271 | 2/1975 | Hoefer ..................................... 204/456 |
| 3,927,826 | 12/1975 | Anderson et al. ....................... 204/456 |
| 3,956,099 | 5/1976 | Israel et al. . |
| 3,980,546 | 9/1976 | Caccavo . |
| 4,048,049 | 9/1977 | Hoefer . |
| 4,337,131 | 6/1982 | Vesterberg . |
| 4,374,723 | 2/1983 | Vesterberg . |
| 4,375,401 | 3/1983 | Catsimpoolas . |
| 4,834,854 | 5/1989 | Sugihara et al. . |
| 4,844,786 | 7/1989 | Sugihara et al. . |
| 4,908,112 | 3/1990 | Pace ........................................ 204/450 |
| 5,051,162 | 9/1991 | Kambara et al. . |
| 5,190,629 | 3/1993 | Sugihara et al. . |
| 5,332,480 | 7/1994 | Datta et al. ............................. 204/601 |
| 5,483,075 | 1/1996 | Smith et al. . |
| 5,529,679 | 6/1996 | Takahashi et al. . |
| 5,584,982 | 12/1996 | Dovichi et al. ......................... 204/603 |
| 5,616,228 | 4/1997 | Nasu et al. .............................. 204/461 |
| 5,730,850 | 3/1998 | Kambara et al. ....................... 204/452 |
| 5,833,826 | 11/1998 | Nordman ................................. 204/452 |
| 5,885,430 | 3/1999 | Kernan et al. .......................... 204/453 |
| 5,900,132 | 5/1999 | Keenan et al. ......................... 204/603 |
| 5,903,348 | 5/1999 | Melman et al. ........................ 204/451 |

FOREIGN PATENT DOCUMENTS

| | | |
|---|---|---|
| 0 280 567 | 8/1988 | European Pat. Off. . |
| 0 475 555 | 3/1992 | European Pat. Off. . |
| 30 34 899 | 4/1982 | Germany . |

*Primary Examiner*—Robert J. Warden, Sr.
*Assistant Examiner*—Andrew Aldag
*Attorney, Agent, or Firm*—Sterne, Kessler, Goldstein & Fox P.L.L.C.

[57] ABSTRACT

A compact, low cost, automated electrophoresis apparatus provides for the optical detection of multiple DNA samples. A substantially cylindrical gel cartridge houses multiple sample lanes that are sealed on the outer periphery by a shrink tube, which allows for straightforward gel casting, as well as for the pre-casting of sequencing gels. The radial column design of the gel cartridge also facilitates the use of a light source to illuminate one or more sample lanes at the same time. The radial column design further provides for an increased sample lane depth that allows for reading through a greater optical path length of the migrated samples, yielding greater optical signal strength, and an increased signal to noise ratio. The gel lanes can be designed to vary in depth as a function of longitudinal length, allowing for a variable current density. Additionally, this radial design allows for different types of optical detection techniques to be performed on the sample, including transmittance and fluorescence. A system of cooling channels incorporated into the radial column design allows for a coolant to be recirculated in the cooling channels between the actual running sample lanes for better lane-to-lane thermal control. This cooling system allows higher operating voltages and facilitates the use of multiple thermal zones, as required, for instance, for single-strand conformation polymorphism (SSCP) applications.

35 Claims, 6 Drawing Sheets

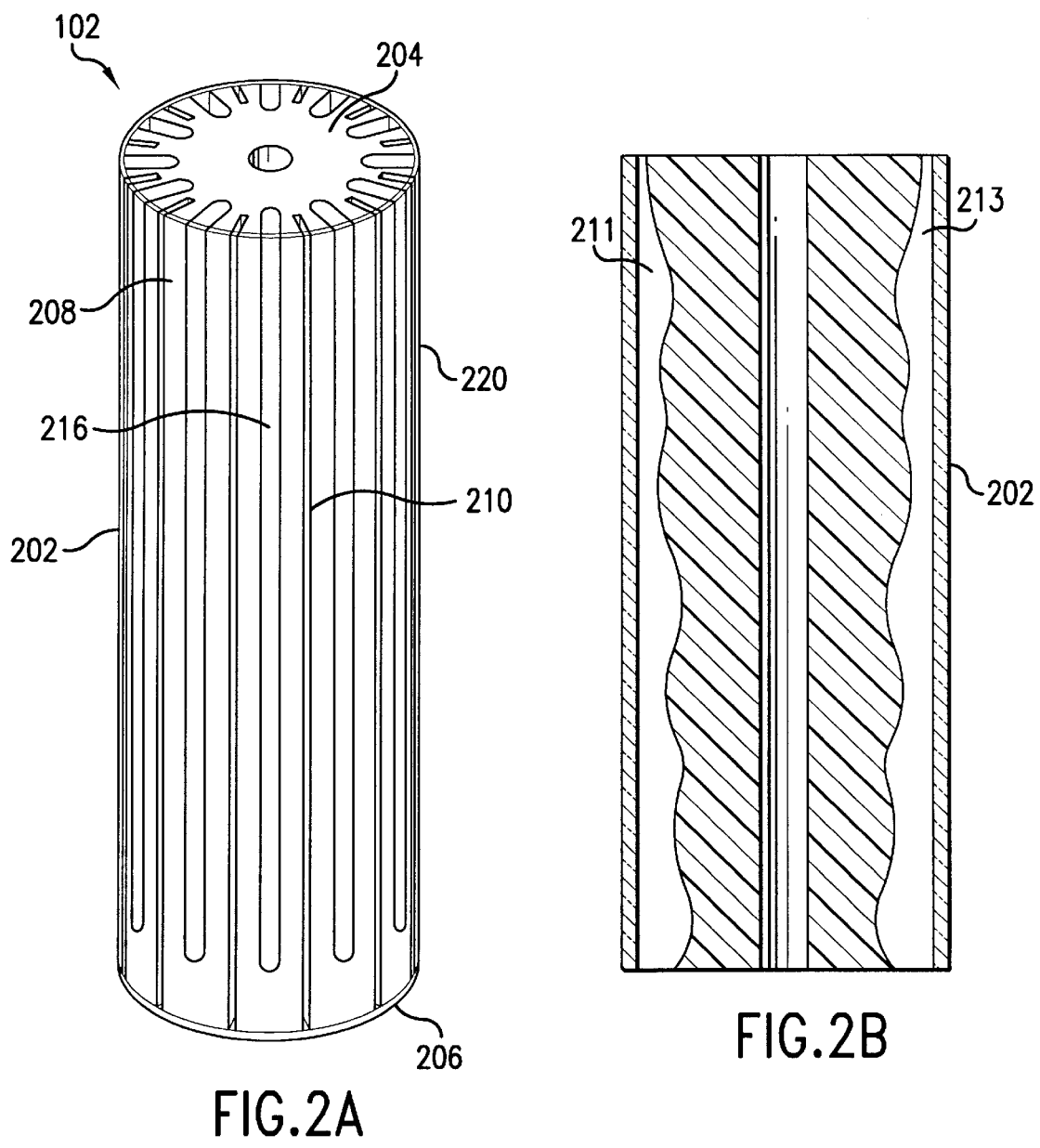

ELECTROPHORESIS SEQUENCING APPARATUS

BACKGROUND OF THE INVENTION

1. Field of the Invention

The present invention is directed to an automated DNA sequencer or forensics device that holds an electrophoretic gel.

2. Related Art

Electrophoresis devices process samples containing DNA and/or protein fragments in carrier media, such as separation gels, for reading a sequence of a particular sample by, for example, optical detection methods. In a typical optical detection technique, fluorescence-labeled DNA fragments are migrated in gel slabs and then excited with a light source at one wavelength to produce a fluorescence signal at another wavelength that corresponds to a particular DNA fragment.

Electrophoresis has conventionally been performed using a "gel sandwich" which comprises two glass plates separated by a small gap distance. The gap is used to hold an agarose or acrylamide/polyacrylamide gel in which the electrophoretic separation occurs. The gap distance defines the thickness of the gel lanes of the gel sandwich. For example, the LTI S2 manual sequencer, distributed by Life Technologies Inc., of Rockville Md., utilizes gel lanes on the order of 0.016 inches (or about 0.4 millimeters (mm)) thick, and approximately 0.2 inches in width. Smaller gel plate gap distances are generally preferred in apparatuses utilizing small gel pore sizes, with preferable gap distances being on the order of 0.1 mm to 3 mm. See, e.g., U.S. Pat. No. 5,529,679 issued to Takahashi et al. ("Takahashi"). Larger gap distances are less desired because they require higher operational voltages to be applied to the electrophoretic gel, resulting in greater heating. Other conventional sequencers include capillary devices, such as that described in the Takahashi patent, and devices that utilize thin, ribbed plastic sheets to hold the electrophoretic gel, such as that described in U.S. Pat. No. 4,374,723 to Vesterberg.

The operation of a conventional gel sandwich takes place as follows. DNA fragments are placed in "wells" formed at the top end of the gel sandwich. These wells are typically formed by the use of a comb that defines the width and number of gel lanes. A voltage is then applied across the gel. The voltage causes particle separation of the sample to occur as a function of the pH and pore size of the gel, the cross section of the gel, the molecular size and charge of the sample, and the applied voltage.

A laser/reader can be configured at the bottom of the standard sequencer gel sandwich to scan back and forth to detect fluorescence. As the DNA bands develop in the electrophoresis process and travel past the detection point, the laser excites individual bands and a sensor reads the bands by scanning the fluorescence as each band passes the reading point.

SUMMARY OF THE INVENTION

The present invention generally relates to a device to be used in an electrophoresis process. In particular, the present invention provides an electrophoresis apparatus comprising a substantially cylindrical cartridge having a plurality of longitudinal gel slots disposed on a peripheral surface of the cartridge. Each gel slot is designed to hold an electrophoretic gel and to receive, for example, a DNA fragment sample. The cartridge can also include a plurality of cooling channels disposed on the peripheral surface. A sleeve is configured to cover the peripheral surface of the column to seal the gel slots and the cooling channels at the peripheral surface. The cartridge can be at least partially immersed in a container containing conductive buffer solution that is divided into two chambers, wherein buffer solution in each chamber is coupled to a voltage source, which provides the current for the electrophoresis process. The sample placed at the top of a gel slot will migrate along the slot at a rate proportional to the molecular size and charge.

According to a preferred embodiment of the present invention, a central cooling column provides a flow path of coolant from an external reservoir through the central region of the cartridge and to each of the cooling channels disposed on the peripheral surface. This design provides for a recirculation of coolant through the device in order to control the temperature of the gels cast in the gel slots. In a preferred embodiment, each of the cooling channels is interleaved and placed equidistant between two of the gel slots. Because the cartridge can be machined or made from an injection molded material, the gel slots and the cooling channels can be designed to conform to a user's specific sequencing applications. For example, the gel slots can be designed to provide a longer optical path length than can be achieved in conventional electrophoresis devices, thus providing higher signal strength and resolution of the band structure from the migrated sample. In addition, the depth of the gel slots can be designed to vary as a function of gel slot length in a controlled manner to facilitate a variable current density at various regions along each of the gel slots, allowing the gel cast in a gel slot to function as a gradient gel.

In another embodiment of the present invention, the electrophoresis device includes a light source receptacle to house a light source or other means of exciting the samples being separated. A plurality of light passages allows the light source to illuminate a migrated band or fragment at a predetermined exposure area. Inexpensive optical detector equipment can be utilized to view migrated samples from each gel slot simultaneously. A processor can be used to process an electrical signal corresponding to the detected transmittance or fluorescence of the illuminated sample.

It is a feature of the present invention that the gel cartridge has a radial design. An advantage of this design is that samples having migrated down the gel slots can be illuminated through a radial length of the sample. As compared to the conventional gel sandwich, this radial approach provides a greater amount of sample for optical detection and, as a result, provides an order of magnitude higher signal to noise ratio over conventional devices. It is a further advantage of the present invention that one light source can illuminate samples from all of the gel slots at the same time. It is yet a further advantage of the present invention that low cost, real-time detection equipment can be used.

It is a further feature of the present invention that the gel cartridge can be machined from ceramic material or made from an injection molded material.

It is yet a further feature of the present invention that the radial column design allows buffer to be recirculated in cooling channels between the actual running gel slots for better slot-to-slot thermal control. It is an advantage of this design that higher operating voltages and faster sample runs can be achieved. Further, the gel slots can be segregated into groups, where each group of slots can be run at a different temperature, which is desirable for single-strand conformation polymorphism (SSCP) applications.

It is still a further feature of the present invention that the radial column design allows the gel slots to be cast by simply sealing the entire peripheral surface of the column with shrink tubing, such as PVC, polyethelene, or TEFLON® [PTFE]. It is an advantage of the present invention that pre-cast gels can be supplied to a user without the bulk and fragility of a glass plate gel.

It is an advantage of the present invention that the radial column design allows the gel slots to vary in depth over the length of the slot. This effectively varies the current density at various points along each of the gel slots and allows the gel slots to function as a gradient gel without the need for the complex formulations, methods, and devices conventionally used for casting actual gradient gels.

It is still a further advantage of the present invention that all gel slots may be easily loaded via marked and funneled loading cups at the top of the slots. Moreover, due to the radial nature of the design, the cartridge may be adapted for automated loading. Combs are unnecessary with the radial design of the present invention.

Further features and advantages of the present invention, as well as the structure and operation of various embodiments of the present invention, are described in detail below with reference to the accompanying drawings.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

FIG. 2A is a perspective view of the gel cartridge assembly according to an embodiment of the present invention;

FIG. 2B is a perspective view of the gel cartridge assembly and gel slots having a varying depth as a function of longitudinal length according to an embodiment of the present invention.

DETAILED DESCRIPTION OF THE PREFERRED EMBODIMENTS

Overview

Figure 1:
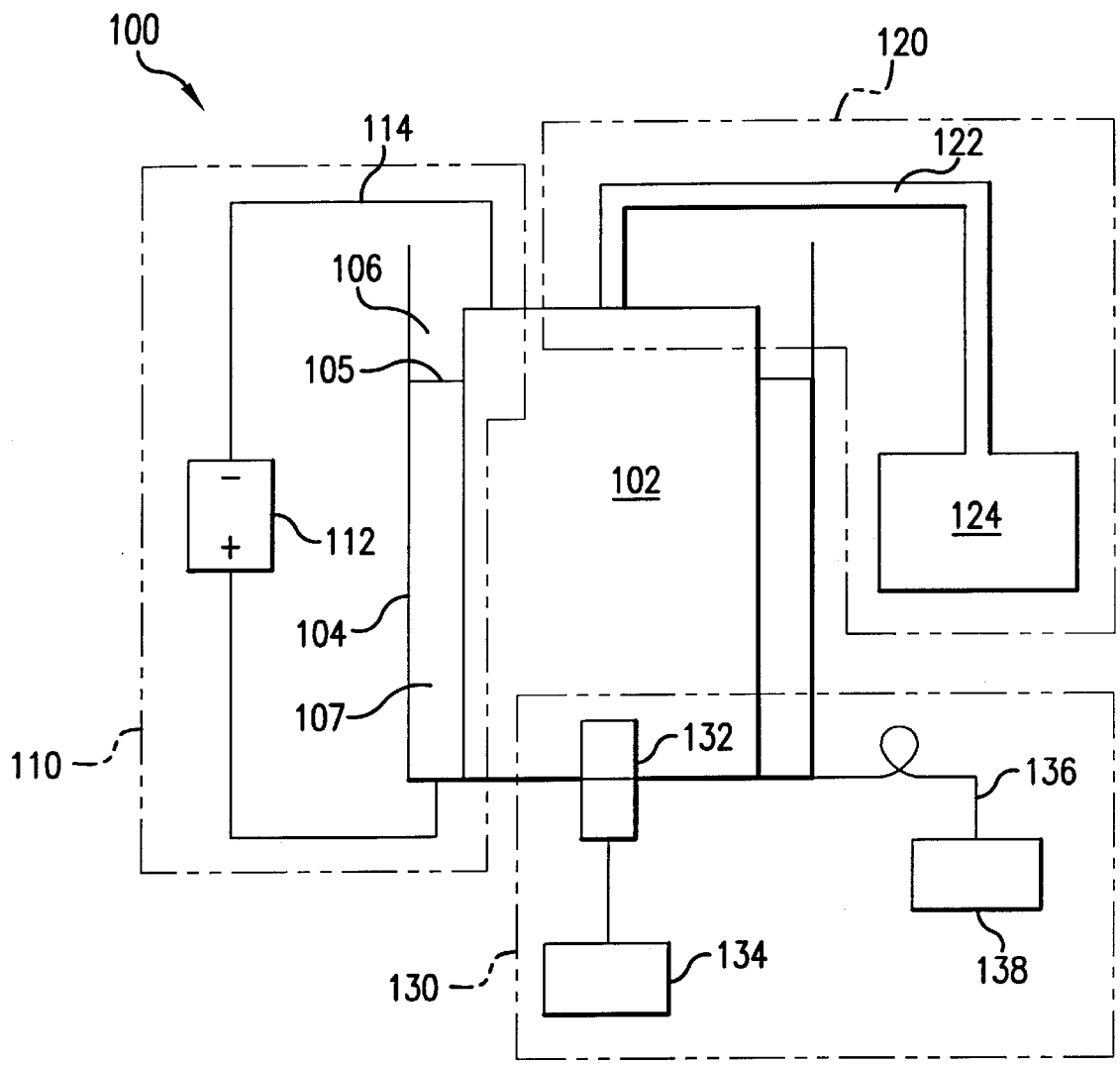
FIG. 1 is a schematic diagram of the electrophoresis apparatus according to a preferred embodiment of the present invention.

The inventors have discovered several deficiencies involving conventional electrophoresis apparatuses. One disadvantage of the conventional "gel sandwich" device is that the laser component of the laser/reader must be focused through one of the thick glass plates onto a spot much smaller than the width of the migrated DNA band. This excitation and detection technique provides less than optimal optical resolution of the band structure. Further, in order to examine multiple samples, expensive laser scanner detection equipment is often required and problems are encountered when scanning multiple samples through the thick glass.

Another disadvantage of the conventional "gel sandwich" device is that the glass plates utilized to seal the gel are required to be very flat. However, most glass plates are subject to slight deformations and bending which causes a slight change in the thickness of the separation gel at a given point along the gel lane. This differential in gel thickness results in an uncontrolled change in the current density at that location in the gel lane, which in turn causes a change in the migration rate of the DNA band or protein fragment. In other words, a band in one gel lane may run at a different rate than a band in an adjacent gel lane.

Moreover, because typical gel sandwiches use glass plates anywhere from 12 inches to 18 inches in width and 12 inches to 15 inches in height, large temperature differences can be created across the plates. The DNA bands migrating in gel lanes located near the outside edges of the plates (where the gap spacers are typically located) may migrate at different rates than the DNA bands migrating in the gel lanes located in the center region of the gel sandwich due to changes in temperature. This visual effect of this thermal differential effect is often referred to as "smiling." Thus, even cooling across both the front and rear glass plates of a conventional device is required to prevent "smiling." Typical air cooling and submersion cooling methods often do not completely resolve this problem. Moreover, conventional gel sandwiches themselves are expensive devices and do not provide potential customers with a pre-cast sequencing gel.

As mentioned above, sample migration rates vary as a function of, for example, particle size and current density. Often, it is desirable to achieve a banding pattern where there is a sufficient spacing or separation between individual bands migrated in a gel lane (e.g., in order to prevent the "bunching" of larger molecules, especially near the top of the gel lane). Several conventional approaches have been developed to provide better separation. For example, "gradient gels" having a varying density can be used in conventional gel sandwiches to affect the rate of separation of the molecules therein. However, gradient gels are much more expensive than standard separation gels. Alternatively, another technique involves varying the spacing between the glass plates of a conventional gel sandwich so that the cross-sectional area of a standard sequencing gel varies from the top of the gel to the bottom of the gel. This is usually achieved by placing a wedge-shaped gel plate spacer between the glass plates, instead of the standard uniform thickness spacer, such that the gel plates are no longer in parallel. This resulting variation in cross-sectional area of the gel lanes in turn affects the current density of the gel at a given point along the gel lane, thus changing the sample migration rate and the separation of the molecules. In other words, by varying the cross-sectional area of the gel lanes, a standard gel in this gel lane configuration can function in a similar manner to a gradient gel. However, conventional gel sandwiches are ill-suited for this alternative approach due to the physical imperfections of glass plates, as well as the difficulty of making a flared gel plate spacer that allows for the gel sandwich to mate properly and not leak when prepared.

The present invention is directed towards a compact automated electrophoresis apparatus that allows for the optical detection of multiple DNA or protein samples using low cost optical detection equipment. The radial column design provides for a straightforward approach to casting sequencing gels and facilitates the use of a single light source to illuminate migrated samples from all of the sample lanes at the same time. Additionally, this radial design allows for different types of optical detection techniques to be performed on the sample, including transmittance and fluorescence. A system of cooling channels incorporated into the radial column design allows for a coolant to be recirculated in the cooling channels between the actual running sample lanes for better lane-to-lane thermal control. This cooling system allows higher operating voltages, quicker sample runs, and the ability to use multiple thermal zones. The manner in which this is accomplished is described in detail below.

Preferred Embodiments

An overview of the preferred embodiment of the present invention is shown in FIG. 1. An electrophoresis apparatus 100 comprises a gel cartridge assembly 102 that is configured to hold an electrophoretic gel. A container 104 is configured to hold gel cartridge assembly 102 and to contain a conductive buffer solution. The buffer solution is divided into an upper buffer chamber 106 and a lower buffer chamber 107 by a divider 105. An electrical subsystem 110 provides an electrical potential that can be applied to the electrophoretic gel housed in gel cartridge assembly 102. The respective poles of a voltage source 112 are coupled to the upper and lower buffer chambers via electrical conduits 114. When voltage source 112 is turned on, a current runs through the gel housed in gel cartridge assembly 102 in order to perform electrophoresis of a sample contained in the gel.

The operating temperature of gel cartridge assembly 102 is controlled by cooling subsystem 120. An external reservoir 124 provides a source of coolant that can be delivered to gel cartridge assembly 102 via coolant flow hose 122. Alternatively, an internal reservoir (not shown) can also be utilized.

Electrophoresis apparatus 100 also includes an optical subsystem 130. A light source 132 simultaneously illuminates samples that have migrated along each of the gel slots (described below) of gel cartridge assembly 102. Light source 132 is powered by a power supply 134. For example, an optical fiber 136 can couple light transmitted through a migrated sample to a low cost optical sensor 138. As described below in connection with FIGS. 5A and 5B, the transmittance or fluorescence of multiple samples can be viewed simultaneously according to the present invention.

FIG. 2A shows an embodiment of gel cartridge assembly 102 according to the present invention. Gel cartridge assembly 102 comprises a cylindrical gel cartridge 202 and a sleeve 220. Gel cartridge 202 is preferably a cylinder having a top surface 204, a bottom surface 206, and a peripheral surface 208. Gel cartridge 202 can be designed to have any practical cylinder diameter and length. Preferably, gel cartridge 202 has a diameter of approximately 1 to 2 inches and a longitudinal length of approximately 6 to 12 inches, depending on the parameters of the electrophoresis experiment to be performed. In a preferred embodiment of the present invention, gel cartridge 202 has a plurality of longitudinal channels 210, referred to as a gel slots, disposed on peripheral surface 208. In addition, a plurality of cooling channels 216, can also be disposed longitudinally on peripheral surface 208 of gel cartridge 202. In another embodiment of the present invention, gel cartridge 202 would be configured to have a single gel slot 210 and optionally one or more cooling channels 216 disposed on peripheral surface 208.

Gel slots 210 are configured to hold a conventional electrophoretic gel, such as an agarose or polyacrylamide gel. Gel is cast in gel slots 210, wherein a voltage can be applied longitudinally across the gel to perform electrophoresis. The gel is used to facilitate a separation process of small particles contained in samples, such as protein fragments, DNA fragments, RNA fragments, or any other samples to be separated using electrophoresis. The use of gel slots 210 obviates the need to use conventional combs due to the well-like nature of gel slots 210.

One advantage of the present invention is that gels can be cast in a consistent and straightforward manner. For example, the casting of a gel can be accomplished as follows. First, gel cartridge 202 (with sleeve 220 covering peripheral surface 208, as explained in detail below) can be placed in a container (not shown). An amount of acrylamide gel can be poured into the container. Bottom surface 206 is raised from the floor of the container so that the bottom of each gel slot is exposed to the acrylamide gel. Next, water can be poured into the container. Because the acrylamide gel is lighter than the water, it will rise above the water and fill gel slots 210, until an area near top surface 204 is reached. The meniscus that forms in the gel at the top of each gel slot can be removed by placing a fluid at the top of each gel slot prior to full gel polymerization. Once the gel polymerizes, the excess water is poured out and the excess gel can be removed by cutting it away from gel cartridge 202. The above description is provided for illustration purposes only. Other methods of gel casting will be apparent to those of skill in the art based on the present description.

The width and depth of gel slots 210 can be designed to a user's specifications. For example, gel slots 210 can each have a slot width of approximately 0.016 inches, and a slot depth (i.e., in the radial direction from peripheral surface 208 towards the center of gel cartridge 202) of approximately 0.2 inches (which is shown in FIG. 3B). Of course, the slot depth and width may be longer or shorter, depending on the particular application. For example, the slot width can be further optimized to facilitate the greatest degree of particle separation. As explained in detail below, one of the advantages of the present invention is that the slot depth can be utilized to provide a greater optical path length through the sample than is found in conventional electrophoresis apparatuses. A longer optical path length provides higher signal strength and resolution of the particles contained in the sample.

In addition, the depth of some or all of gel slots 210 can be tapered from top surface 204 to bottom surface 206 in a linear or non-linear fashion in order to achieve a gradient effect. This slot tapering varies the cross-sectional area of each gel slot and thus allows the current density to be varied when voltage is applied, thereby further increasing resolution of the band structure of a particular sample and allowing more base pairs per lane. The radial column design of the present invention allows gel slots 210 to vary in cross-section over the length of the gel slots. This effectively varies the current density at various points along the lane which allows the lane to function as a gradient gel without the need for casting an actual gradient gel material. As explained in detail below, both the depth and width of gel slot 210 can be changed, depending on the experimental parameters desired by a user. For example, as shown in FIG. 2B, gel cartridge 202 comprises gel slots 211 and 213, where the depth of gel slots 211 and 213 each vary in a non-linear manner. Thus, the migration rate of DNA bands or protein fragments will vary as a function of current density at various regions longitudinally along gel slots 211 and 213. Because gel cartridge 202 can be machined from a ceramic material, for example, a standard computer numeric controlled (CNC) machining process can be used to create a gel cartridge comprising gel slots of the same or variable gel slot depths, wherein each gel slot can be individually tapered to the same gel slot depth or differing gel slot depths.

Referring back to FIG. 2A, individual gel slots 210 are isolated from each other with cooling channels 216 between them. For example, gel cartridge 202 can comprise 12 gel slots and 12 separate cooling channels or 24 gel slots and 24 cooling channels, depending on a user's needs. This configuration also provides for a convenient way to load and examine multiple samples. For example, all gel slots 210 may be easily loaded via marked and funneled loading cups or indentations (not shown) at top surface 204 of gel slots 210. Moreover, due to the radial nature of the design, the gel cartridge 202 can be adapted for automated loading as will be apparent to those of skill in the art based on the present descriptions.

Cooling channels 216 provide fluid pathways for a coolant that can be utilized to control the temperature of the gel cast in gel slots 210. For example, the thermal properties of an electrophoretic gel play a major role in an electrophoresis experiment. Typical voltages applied to a gel can reach up to several thousand volts. Sufficient temperature control is highly advantageous because any variance in temperature along the length, or across a gel can change the migration rate of the sample migrating through the gel. Having a plurality of cooling channels disposed on peripheral surface 208 will help prevent the appearance of "hot spots" and "cold spots" in the gel.

In a preferred embodiment of the present invention, each of cooling channels 216 are placed equidistant from each of gel slots 210. This arrangement is an advantage over conventional gel sandwiches in terms of thermal control. The cooling channels help maintain gel slots 210 at a relatively constant operating temperature. Conventional gel sandwiches have multiple "dead spots" between the sample lanes. These dead spots are areas that do not contain any samples, yet still carry a current and generate heat. In the present invention, due to the lack of between slot "dead spots," there are no between slot current losses that produce heat and require larger running currents.

In other embodiments of the present invention, the configuration of cooling channels 216 can be altered so that different groups of gel slots can run at different temperatures. Each of cooling channels 216 can be designed to be of a predetermined width, thus providing more or less coolant flow to different regions of gel cartridge 202. Separate cooling and heating systems can also be utilized to create different temperature zones. These different configurations will be apparent to those of skill in the art based on the present description.

Gel cartridge 202 can be manufactured from a non-conductive material with good thermal properties, such as ceramic or plastic material. In addition, it is preferable that molecular weight markers or fluorescent tags that are often used in electrophoresis do not stick to the material surface. Thus, it is preferred to use a material that possesses this non-stick property or that can be treated by conventional means so that the marker or fluorescent tag does not stick. For example, gel slots 210 and cooling channels 216 can be machined from the peripheral surface of a ceramic cylinder to a desired depth and width by using CNC techniques, as would be apparent to those of skill in the art. Alternatively, gel cartridge 202 can be an injection molded material, shaped by an injection molding technique, well known to those skilled in the art. Thus, using the injection molding technique, the width and depth of gel slots 210 can be controlled to provide a uniform gel slot configuration or to conform with a particular user's specifications. In a preferred embodiment, gel cartridge 202 is made from a reusable and recyclable material. According to the present invention, disposable injection molded gel cartridges may be designed with multiple configurations and gel matrices to be used in forensic tests, for example.

Gel cartridge assembly 102 also comprises a sleeve 220, that is configured to cover peripheral surface 208 in order to seal each of the gel slots 210 and cooling channels 216 at peripheral surface 108. Thus, gel slots 210 are open at both top surface 204 and bottom surface 206. Preferably, gel slots 210 are configured to receive the DNA fragment sample at top surface 204, as discussed above. Preferably, sleeve 220 can be a shrink tube material that will conform to peripheral surface 208 upon application of heat from an external heat source. Sleeve 220 is preferably a plastic or vinyl material that would resist deformation under high operating temperatures. For example, sleeve 220 can be a TEFLON® material, manufactured by the E.I. du Pont de Nemours Company. Other materials, such as PVC and polyethelene can be used as sleeve 220, based on the properties described above. In addition, a second outer sleeve made out of an insulating material (not shown) can be placed over sleeve 220 to facilitate even better thermal control of the gel.

Alternatively, sleeve 220 could be a machined sleeve that substantially conforms to the peripheral surface of gel cartridge 202. For example, gel cartridge 202 can be designed to have a tapered shape, such that the diameter at the top of gel cartridge 202 is slightly longer or shorter than the diameter at the bottom surface. This tapered design would facilitate the ability to machine a more rigid tapered sleeve 220 to slide onto and conform with peripheral surface 208 of gel cartridge 202. Further manners of sealing the peripheral surface of gel cartridge 202 will be apparent to those of skill in the art based on the present description.

Another advantage of the present invention is that pre-cast gels can be supplied to a user. Conventional devices generally require a user to cast a sequencing gel. Thus, a user will not know a priori what the consistency of a gel is, which could be critical in interpreting the results of a sequencing experiment. The present invention can provide a user with a pre-cast gel, where the consistency of the gel has already been tested and determined. For example, based on the gel casting method described above, gel cartridge assembly 102 can be pre-cast by a supplier. In addition, quality control of a gel batch can be assured by testing the consistency of one gel slot before shipping. As opposed to a conventional gel sandwich, where the gel lanes are only separated based on the comb configuration, with gel cartridge assembly 102, all gel slots 210 can be blocked off, except for one gel slot to be used for quality control. This information can be supplied to the user, who can perform electrophoresis based on the standards generated by the supplier. Methods of performing quality control tests will be apparent to those of skill in the art based on the present description.

In addition, because of the compact and rugged nature of gel cartridge assembly 102, the risks that would be inherent in the shipment and delivery of a conventional sequencing apparatus are greatly reduced. Further, because gel cartridge 202 can be made out of a reusable material, after an experiment has been performed, the cartridge can be shipped back to the supplier, cleaned, and then pre-cast for another set of experiments.

Figure 3A:
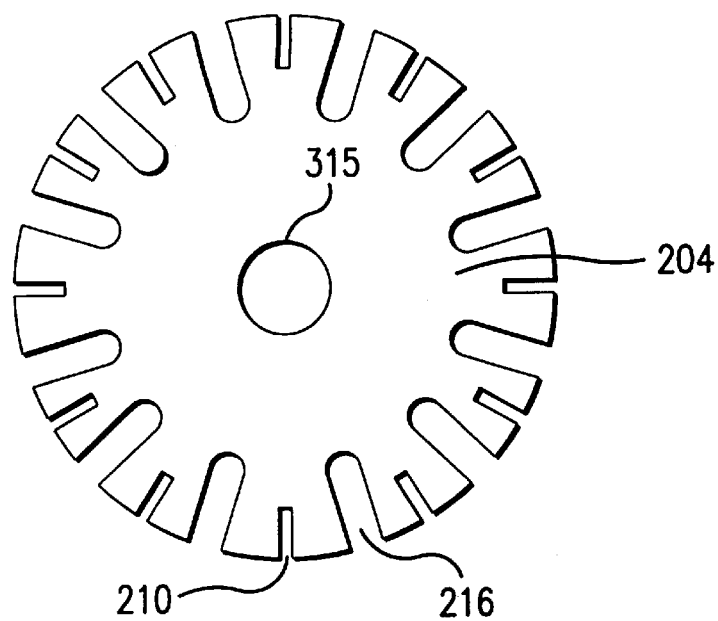
FIG. 3A is a view of the top surface of the gel cartridge according to an embodiment of the present invention.
Figure 3B:
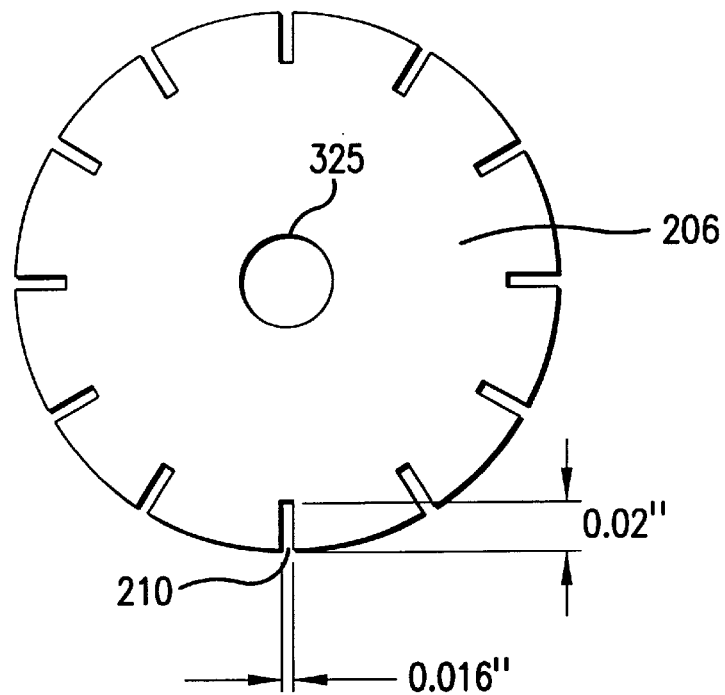
FIG. 3B is a view of the bottom surface of the gel cartridge according to an embodiment of the present invention.

FIG. 3A shows a top view of top surface 204 of gel cartridge 202. A central bore 315, also referred to as a central cooling column, is made in the central region of gel cartridge 202. Central cooling column 315 is open at top surface 204 and provides a coolant flow path through the central region of gel cartridge 202. Also shown in FIG. 3A is a preferred arrangement of gel slots 210 and cooling channels 216, whereby each of cooling channels 216 are interleaved and placed equidistant between two of the gel slots 210 for better slot-to-slot thermal control. An advantage of the present invention is that the radial column design allows coolant to be recirculated from central cooling column 315 to cooling channels 216 via a set of return ports 418 (shown in FIG. 4) located near the bottom region of cooling channels 216. This cooling design allows higher operating voltages.

FIG. 3B shows a more detailed view of bottom surface 206. As shown in FIG. 3B, the width of gel slot 210 is 0.016 inches and the depth of gel slot 210 is 0.2 inches. As mentioned above, other gel slot widths and thicknesses can be utilized depending on a user's specifications. In one embodiment of the present invention, bottom surface 206 can be configured to include a receptacle 325, large enough to house or hold either a light source, multiple light sources, or a radial mirror (not shown). For example, receptacle 325 can be an approximately 0.5 inch diameter bore into gel cartridge 202, having a bore length of approximately 0.5 to 1 inch into the interior of gel cartridge 202. The optical reading embodiment of the present invention is described in further detail in connection with FIGS. 5A and 5B.

Figure 4:
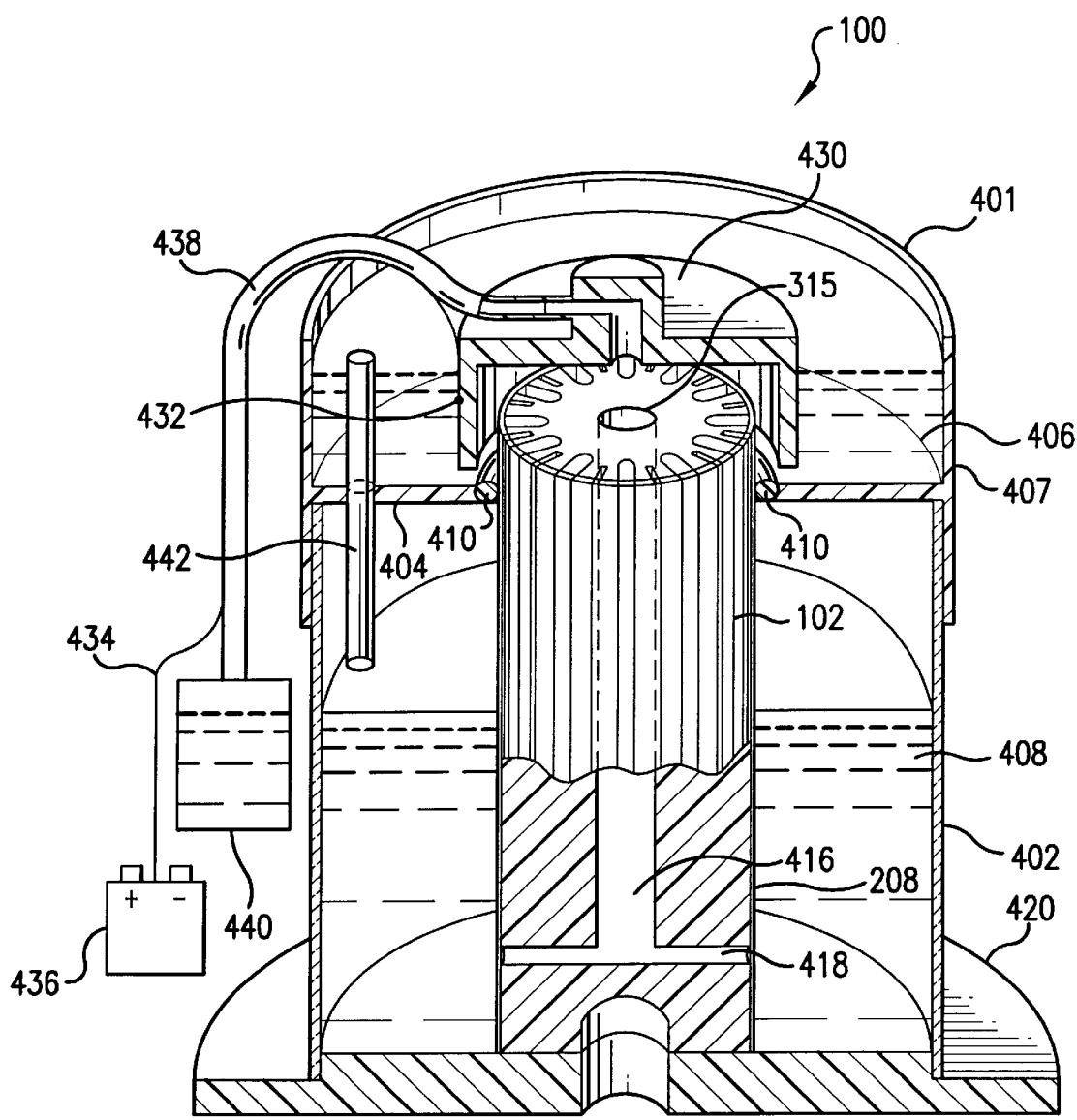
FIG. 4 is a perspective view of the electrophoresis apparatus according to a preferred embodiment of the present invention.

FIG. 4 shows a more detailed illustration of a preferred embodiment of the present invention, electrophoresis apparatus 100. Gel cartridge 202 is placed and held in a container assembly 401. Container assembly 401 is configured to hold a conductive buffer solution. Container assembly 401 has a container wall 402. Container wall 402 can be a glass or plastic transparent tube material such as an acrylic or PLEXIGLASS®. The outer diameter of container wall 402 can be any practical amount, preferably on the order of approximately 2½ to 3 inches. The thickness of container wall 402 can be on the order of approximately 1/16 to ¼ inches, or enough thickness to adequately hold the buffer solution contained therein. The buffer solution can be a buffered saline solution, such that it conducts charge. Other buffer solutions can be utilized, as will be apparent to those of skill in the art based on the present description.

An upper buffer chamber 406 and a lower buffer chamber 408 are separated by a divider 404. Thus, the lower portion of gel cartridge assembly 102 can be at least partially immersed in buffer solution contained in lower buffer chamber 408 and the top portion of gel cartridge assembly 102 can be immersed in buffer solution contained in upper buffer chamber 406. Divider 404 can be a machined plastic or like material that is incorporated onto a top end structure 407. Top end structure 407 is designed to mate onto the top part of container wall 402 and to provide an opening to facilitate the removal of gel cartridge assembly 102. Top end structure 407 provides a reservoir for buffer solution and functions as upper buffer chamber 406. A seal 410 can be configured to mate with both a peripheral surface of gel cartridge assembly 100 and divider 404. Alternatively, seal 410 can be configured to mate with the peripheral surface of gel cartridge assembly 102 and an inner surface of container wall 402 in order to separate the upper and lower buffer chambers.

Seal 410 can be a gasket, a flexible membrane material such as LATEX, or a known O-ring material. Seal 410 is designed to prevent the flow of buffer solution contained in upper buffer chamber 406 from leaking into lower buffer chamber 408. As opposed to conventional devices that exhibit leakage problems, an advantage of the substantially cylindrical design of the gel cartridge of the present invention is that a leak-free seal is more readily attainable. Other means of preventing leakage of buffer solution between the upper and lower buffer chambers will be apparent to those of skill in the art based on the present description.

As discussed above with respect to FIG. 3A, central bore 315 located at top surface 204 provides a central cooling column (shown in FIG. 4 as central cooling column 416) through a central portion of gel cartridge assembly 102. A plurality of return ports or passages 418 provide a coolant flow path from central cooling column 416 to each corresponding cooling channel 216 disposed on the peripheral surface of gel cartridge 202.

Alternatively, gel slots 210 can be segregated in quadrants or other groups, whereby each quadrant may be run at a different temperature by changing the configuration of the cooling channels. This can be accomplished by pumping coolant of differing temperatures through the different quadrants. As mentioned above, separate heating and/or cooling systems (not shown) can be utilized to provide for operating at multiple temperature zones. This type of multiple temperature zone configuration is highly valuable for known sequencing techniques such as SSCP.

A base 420 is configured to mate with a second end of gel cartridge assembly 102 and to maintain gel cartridge assembly 102 in a fixed position within container assembly 401. A base slot or recess (shown in FIG. 5B as recess 527), corresponding to the inner and outer diameters of container wall 402, can be machined onto a top surface of base 420 in order to hold container wall 402 firmly in place. Other means of securing outer wall 402 to base 420 will be apparent to those of skill in the art. Gel cartridge assembly 102 can be supported by base 420 by means of a second recess (shown in FIG. 5B as recess 528) built into base 420. The second recess 528 still allows buffer solution in the lower buffer chamber to be in communication with the bottom end of the gel cast in gel slots 210. In addition, base 420 can be designed to include a plurality of light passages 502 (described below in connection with FIGS. 5A and 5B) recessed into base 420, such that the number of light passages corresponds to the number of gel slots 210 found on gel cartridge 202. Gel slots 210 can be aligned to the plurality of light passages by means of a pin (not shown), or other alignment mechanism that will be apparent to those of skill in the art based on the present description.

Figure 5A:
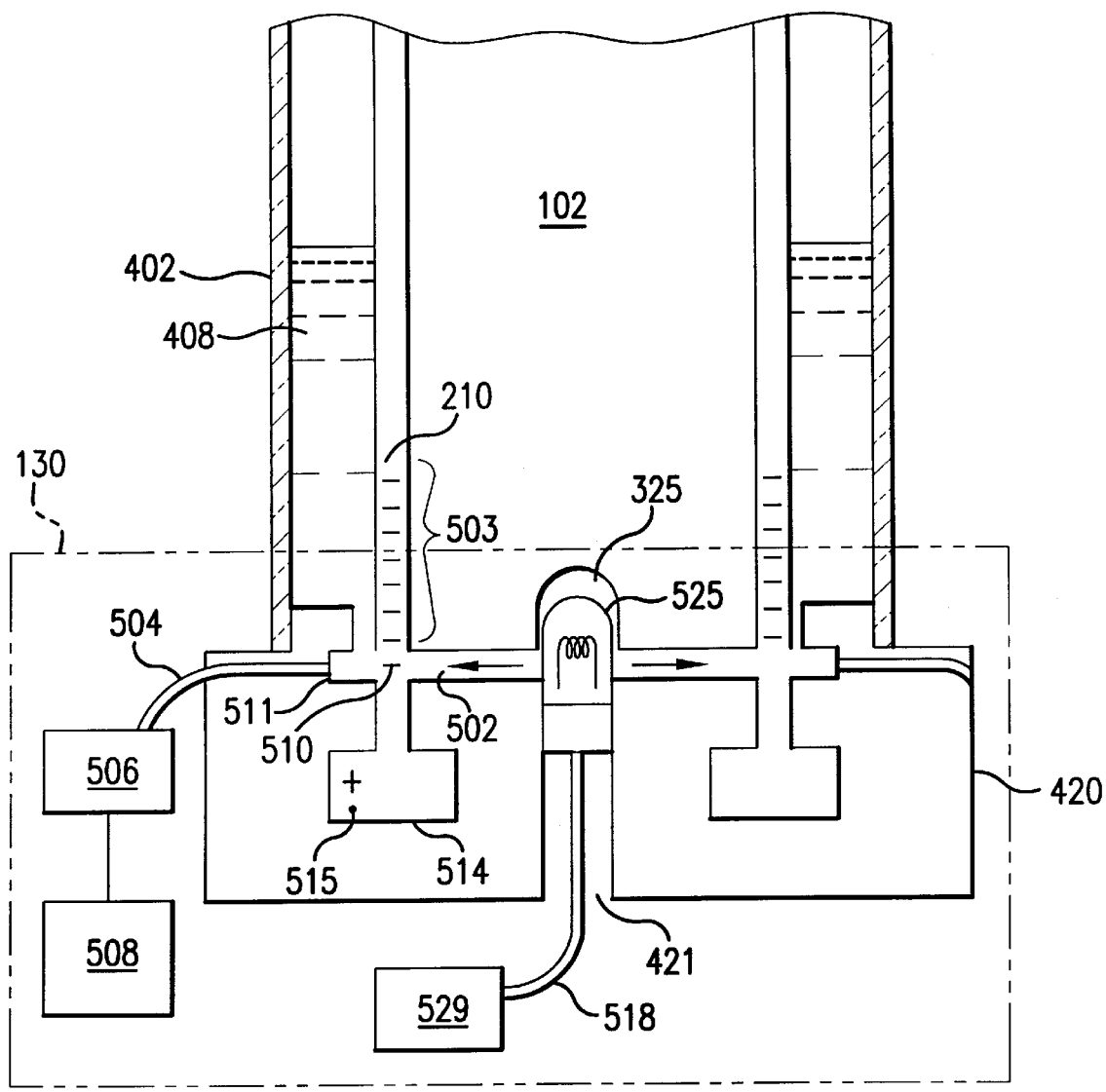
FIG. 5A is a view of an optical detection system used with the electrophoresis apparatus of the present invention.

In addition base 420 is configured with an opening 421 to allow a light source to be situated at or near receptacle 325. As shown in FIG. 5A, light source 525 is coupled to a light source power supply 529 by an electrical conduit or wire 518. Preferably, light source 525 is an ultraviolet or visible wavelength light bulb or lamp, depending on the type of fluorescent tags and markers utilized in the electrophoresis experiment. As explained in detail below in connection with FIG. 5A, light emanating from light source 525 can travel down each of light passages 502 and illuminate migrated samples as they pass a predetermined area 510. Many suitable light sources such as ultraviolet or visible lamps, bulbs, light emitting diodes, or lasers are commercially available and are well known in the art.

Alternatively, a mirror or other reflecting optic can be placed in receptacle 325 to reflect a laser beam or other suitable light source down each of the light passages 502. Opening 421 can be designed to allow the passage of light from the light source to the reflecting optic. Description of this embodiment of the present invention is described in detail in connection with FIG. 5A.

Referring back to FIG. 4, an endcap 430 is configured to mate a coolant flow hose 438 with central bore 315 at top surface 204 of gel cartridge 202. In a preferred configuration, upper buffer chamber 406 is open at the top portion in order to allow placement and removal of endcap 430. In addition, an electrical conductor 432 can be placed on endcap 430 in order to provide a charge for buffer solution contained in upper buffer chamber 406. For example, electrical conductor 432 (here, the cathode) can be a stainless steel or platinum wire or plate that is coupled to one pole of a voltage source 436 via an electrical wire or conduit 434. For example, conductor 432 can be disposed on a peripheral surface of endcap 430 that is in contact with buffer solution held in upper buffer chamber 406. In a similar manner, as shown in FIG. 5A, lower buffer chamber 408 can be connected to another pole of a voltage source 436 via an electrical conductor, such as anode 515, which is housed in well 514. Anode 515 can also be a platinum wire or plate. Other arrangements for coupling the upper and lower buffer chambers to a voltage source will be apparent to those of skill in the art based on the present description.

Endcap 430 is mounted on the top of gel cartridge 202 in such a manner as to allow charged buffer solution contained in upper buffer chamber 406 to be in contact with the electrophoretic gel housed in gel slots 210. Buffer solution is exposed to the opening of gel slots 210 at top surface 104. Similarly, gel cast in gel slots 210 at the bottom surface 106 of gel cartridge 202 contacts buffer solution contained in lower buffer chamber 408.

In a preferred embodiment of the present invention, the buffer solution contained in upper buffer chamber 406 has a net negative charge applied to it, thus acting as a cathode. Buffer solution contained in lower buffer chamber 408 would then have a positive net charge applied to it, acting as an anode. Current then runs longitudinally through the electrophoretic gel cast in gel slots 210. In this embodiment, samples placed in the gel would migrate from "top to bottom." Alternatively, electrophoresis apparatus 100 can also be designed to run samples from "bottom to top" as would be apparent to those of skill in the art based on the present description.

A coolant flow hose 438 can be in fluid communication with an external coolant reservoir 440 or an internal reservoir (not shown). This arrangement provides for a recirculation of buffer or an additional source of coolant for central cooling column 315. This configuration facilitates coolant to circulate through gel cartridge 202 in order to control operating temperatures. In a preferred embodiment of the present invention, coolant that is used to control the temperature of the gel housed in gel slots 210 is the same type of buffer solution that is also contained in upper buffer chamber 406 and lower buffer chamber 408. In addition, a buffer solution overflow conduit 442 can be provided to allow an overflow of buffer solution from the upper buffer chamber 406 into lower buffer chamber 408. In one embodiment of the present invention, overflow conduit 442 comprises a tube that provides a gravity drip path from upper buffer chamber 406 into lower buffer chamber 408, such that the charge characteristics of either buffer chamber are not affected. Other means for relieving an overflow of buffer solution will be apparent to those of skill in the art based on the present description.

Figure 5B:
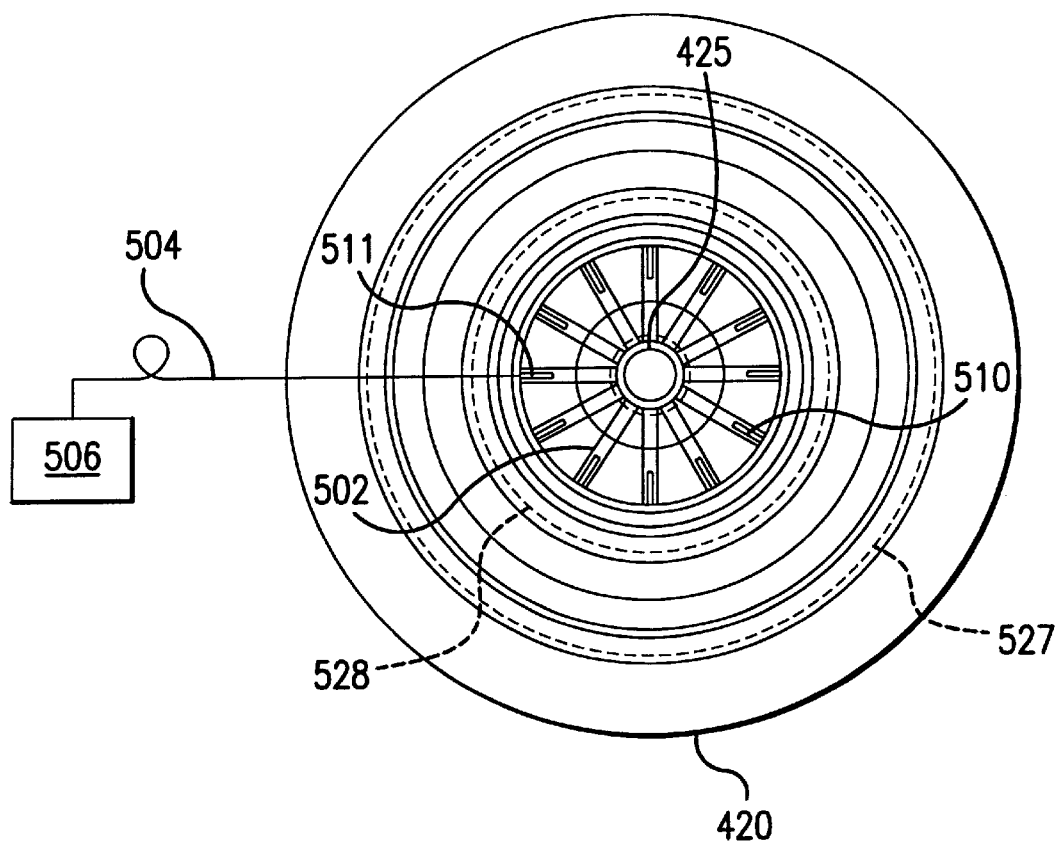
FIG. 5B is a top view of the base of the electrophoresis apparatus according to an embodiment of the present invention.

FIG. 5A shows the optical subsystem 130 of the present invention. FIG. 5B shows a top view of base 420. As shown in FIG. 5B, base 420 is configured to have a plurality of light passages 502 corresponding to the number of gel slots included in gel cartridge assembly 102. In FIG. 5A, only one gel slot 210 is shown for convenience purposes.

Referring to FIG. 5A, for example, light source 525 can be turned on to illuminate light passage 502. Light passage 502 passes light from light source 525 through buffer solution to a predetermined exposure area 510. As a particular DNA band exits the bottom of gel slot 210, the band enters buffer solution and continues a migration towards anode 515, which can be housed in well 514, that is also recessed into base 420. The light emitted from light source 525 can then pass through the length of a DNA band, which corresponds to the depth of gel slot 210. In this embodiment, a gel slot depth of 0.2 inches corresponds to the approximate length of the DNA bands that have been separated by electrophoresis (shown in FIG. 5A as banding pattern 503). Because the depth of gel slots 210 can be approximately 0.2 inches, the present invention provides a longer optical path length (0.2 inches) through the sample than is achieved in a conventional "gel sandwich" device, where laser/readers gather fluorescence signal emitted from the width (0.016 inches) of the DNA band.

In this embodiment, a fiber optic light pipe 504 is mounted to a point inside base 420 at a location 511. Light pipe 504 can extend through an interior region of base 420 to sensor 506. Leakage of buffer solution can be prevented by using an o-ring seal, as will be apparent to one of skill in the art. Light transmitted through the DNA band of interest is coupled into light pipe 504 and is detected by a sensor 506. Light pipe 504 can be a single multi-mode optical fiber or can comprise a bundle of optical fibers, depending on the amount of light required to be coupled into sensor 506. In a preferred embodiment, a plurality of fiber light pipes 504 corresponding to the number of light passages 502, can be mounted inside base 420, so that multiple samples may be detected simultaneously. For example, if gel cartridge 202 has 12 gel slots, 12 separate light pipes 504 can be utilized. Each light pipe 504 would be mounted inside base 420 corresponding to the exposure area. An additional advantage of this type of illumination arrangement is that light is incident upon only one DNA band per gel slot at any given time (i.e., light is not directed up into the gel slots). Thus, spurious signals emanating from other DNA bands housed in the same gel slot are minimized.

Sensor 506 receives an amount of light transmitted through the sample of interest contained in the electrophoretic gel and generates an electrical signal corresponding to that amount of transmitted light. For example, a circuit board comprising a plurality of sensors 506 corresponding to the number of gel slots 210 and light pipes 504 can be designed to view multiple samples simultaneously, as would be apparent to those of skill in the art. In addition, a wavelength selective filter (not shown) can be utilized to filter out unwanted wavelengths of light and to allow wavelengths of interest (such as the fluorescence band wavelengths of particular DNA tags) to pass to sensor 506. For transmittance viewing, a baseline amount of light transmitted through the buffer solution can be easily measured. Thus, by knowing the absorption characteristics of various DNA (or protein) fragmentary samples, the degradation of an amount of transmitted light signal coming from light source 525 at a particular wavelength can be determined. This electrical signal can then be processed by a processor 508. Because the length of the DNA bands, corresponding to the depth of gel slots 210, is on the order of 0.20 inches, a substantial amount of degradation of the light signal emitted from light source 525 can be detected by sensor 506.

Alternatively, a small flourescent tag, marker, or label (such as a fluorescein isothiocyanate fluorophore, or a succinyl fluorescein fluorophore, etc.) may be placed on the sample of interest. In that particular case, the light emitted from light source 525 will excite the flourescent tag, thereby causing a fluorescence at a particular wavelength. This fluorescence would be coupled into sensor 506 via light pipe 504 and a wavelength selective filter.

One of the advantages of the present invention is that inexpensive detectors can be used to sense the fluorescence or transmittance of multiple samples. Sensor 506 can be a charged coupled device (CCD), a PIN photodiode, or an avalanche photodiode, which are widely available. Thus, DNA (or protein) bands are read through their length, which corresponds to the depth of the gel slot (0.2 inches), as opposed to the gel slot width (0.016 inches), for an order of magnitude higher signal to noise ratio, while still using low cost, real-time detection equipment.

Alternatively, other illumination arrangements can be utilized to provide higher photodetecting efficiency. For example, an ultraviolet or visible laser can be utilized as light source 525, and can be mounted below base 420. The laser can be selected to operate at a wavelength corresponding to the absorption of a fluorescent tag. The laser beam can travel through opening 421. A mirror can be designed to reflect the incident laser beam outward along a plurality of directions defined by light passages 502. Thus samples running in each of the gel slots can be illuminated by the reflected laser beam. The fluorescence (or transmittance) can then be collected by the plurality of light pipes 504, and detected as described above. In addition, imaging optics (such as spherical or cylindrical lenses) can also be utilized to further improve the optical signal strength.

Thus, the design of the electrophoresis apparatus of the present invention offers the advantage of no moving parts in the optical detection system, such as scanners and moving lasers found in conventional sequencer devices. Additionally, the present invention provides the flexibility to view multiple samples from either a single gel slot, or from a plurality of gel slots simultaneously.

FIG. 5B shows a top view of base 420. In this embodiment, 12 light passages (corresponding to 12 gel slots), as illustrated by light passage 502, can be recessed onto the top surface of base 420. A single light source 425 can be used to illuminate all 12 light passages 502. The DNA bands exit from the bottom of each of the gel slots and are illuminated over exposure area 510. Note that after being illuminated, the DNA band continues to move through the buffer solution towards anode 515 (shown in FIG. 5A). A plurality of light pipes, as illustrated by light pipe 504, can be mounted near the exposure area, such as at location 511, to couple the transmittance or fluorescence from the illuminated DNA band. This optical signal is then received by sensor 506, as discussed above.

Referring back to FIG. 5A, processor 508, which can be a conventional microprocessor such as those found in personal computers, can be programmed with conventional DNA image analysis software, which is widely available from a variety of vendors including Eastman Kodak Inc., of Rochester N.Y. Data output from processor 508 can be in the form of a TWAIN file, a known image output file that is conventionally used.

Conclusion

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all articles and patent documents mentioned above are incorporated by reference herein.

What is claimed is:

1. An electrophoresis apparatus, comprising:
   a gel cartridge assembly, including,
      a substantially cylindrical column having a longitudinal first channel disposed on a peripheral surface of said column;
      a longitudinal second channel disposed on said peripheral surface of said column for providing a flow of coolant to control a temperature of an electrophoretic gel placed in said first channel;
      means for providing a flow of coolant to said second channel;
      a sleeve configured to cover said peripheral surface of said column and seal said first channel at said peripheral surface, said sealed first channel being configured to receive said electrophoretic gel; and
   a container configured to hold said gel cartridge assembly and first and second quantities of a buffer solution, wherein said first quantity of buffer solution and a first end of said gel cartridge assembly are in contact and wherein said second quantity of said buffer solution and a second end of said gel cartridge assembly are in contact to facilitate electrophoresis of a sample contained in said electrophoretic gel.

2. The apparatus of claim 1, further comprising:
   a plurality of longitudinal first channels disposed on said peripheral surface of said column to receive said electrophoretic gel; and
   a plurality of longitudinal second channels disposed on said peripheral surface of said column, each of said second channels being interleaved between two of said first channels and being configured to receive said flow of coolant.

3. The apparatus of claim 2, wherein each of said second channels is spaced equidistant from each of said first channels.

4. The apparatus of claim 2, wherein a depth of said first channels varies over said length.

5. The apparatus of claim 2,
   wherein each of said channels is open at said first end and closed at said second end, and wherein said means for providing a flow of coolant comprises:
      a central bore in said column open at a first end of said column and closed at a second end of said column;
      a plurality of passages in said column, each passage connecting a corresponding second channel to said central bore adjacent said second end of said column, said plurality of passages providing a coolant flow path between said second channels and said central bore.

6. The apparatus of claim 5, wherein each of said second channels is of a predetermined width, and wherein a predetermined number of said plurality of first channels and said second channels is selected to form a group such that the apparatus comprises a plurality of groups, and wherein an analysis of samples in each of said groups is performed at a different temperature.

7. The apparatus of claim 1, further comprising:
   a seal configured to mate with the peripheral surface of said gel cartridge assembly and an inner surface of said container to divide said container into a first container portion containing said first quantity of buffer solution and a second container portion containing said second quantity of buffer solution; and
   a base configured to mate with said second end of said gel cartridge assembly to maintain said second end of said gel cartridge assembly in a fixed position within said container.

8. The apparatus of claim 7, wherein said seal is a flexible membrane that seals around said gel cartridge assembly.

9. The apparatus of claim 7, wherein said first container portion further comprises:
- a port to allow a flow of said buffer from an external reservoir; and
- means for relieving an overflow of buffer solution from said first container portion.

10. The apparatus of claim 7, further comprising:
- an electrical contact in communication with a voltage source to provide an electrical voltage across said first and second quantities of buffer solution.

11. The apparatus of claim 10, further comprising:
- an end cap configured to mate a coolant flow hose with said central bore at said first end of said column;
- a first electrical conductor connected to said end cap; and
- a second electrical conductor connected to said base.

12. The apparatus of claim 11, wherein said first container portion houses said first electrical conductor.

13. The apparatus of claim 11, wherein a platinum wire couples said first container portion to said voltage source, such that when said voltage source is turned on, a current flows through said gels in said plurality of first channels to said second container portion.

14. The apparatus of claim 1, further comprising:
- a receptacle located at a selected end of said column to house a light source.

15. The apparatus of claim 1, wherein said column is formed by a process selected from the group consisting of machining, extruding, and injection molding.

16. The apparatus of claim 1, wherein said column is manufactured from a ceramic material.

17. An electrophoresis apparatus, comprising:
- a gel cartridge assembly, including,
  - a substantially cylindrical column having a longitudinal channel for receiving an electrophoretic gel, said channel being disposed on a peripheral surface of said column, wherein a depth of said channel is greater than a width of said channel;
  - a sleeve configured to cover said peripheral surface of said column and seal said channel at said peripheral surface;
- a container configured to hold said gel cartridge assembly and first and second quantities of a buffer solution, wherein said first quantity of buffer solution and a first end of said gel cartridge assembly are in contact and wherein said second quantity of said buffer solution and a second end of said gel cartridge assembly are in contact to facilitate electrophoresis of a sample contained in said electrophoretic gel;
- a seal configured to mate with the peripheral surface of said gel cartridge assembly and an inner surface of said container to divide said container into a first container portion containing said first quantity of buffer solution and a second container portion containing said second quantity of buffer solution; and
- a base configured to mate with a second end of said gel cartridge assembly to maintain said second end of said gel cartridge assembly in a fixed position within said container.

18. The apparatus of claim 17, comprising:
- a plurality of longitudinal channels disposed on said peripheral surface of said column to receive said electrophoretic gel, wherein at least one of said plurality of longitudinal channels has a depth greater than a width.

19. The apparatus of claim 18, wherein a depth of each of said channels varies over each of said lengths.

20. The apparatus of claim 17, further comprising:
- a receptacle located at a selected end of said column to house a light source.

21. The apparatus of claim 20, wherein said selected end of said column further comprises:
- a light passage to facilitate passage of light from said light source to a predetermined exposure area of said longitudinal channel.

22. The apparatus of claim 21, further comprising:
- a sensor to receive an amount of light transmitted through a sample at said predetermined exposure area and to generate an electrical signal corresponding to said amount of light;
- a fiber optic cable to couple said amount of light to said sensor; and
- a processor to process said electrical signal from said sensor.

23. The apparatus of claim 22, wherein said sensor is selected from the group consisting of a charge-coupled device (CCD), a PIN photodiode, and an avalanche photodiode.

24. The apparatus of claim 22, further comprising:
- a wavelength selective filter to filter out unwanted wavelengths of light and to allow wavelengths of interest to pass to said sensor.

25. The apparatus of claim 20, further comprising:
- a plurality of longitudinal channels disposed on said peripheral surface of said column; and
- a plurality of light passages, each light passage facilitating passage of light from said light source to a predetermined exposure area of a corresponding one of said longitudinal channels.

26. The apparatus of claim 25, further comprising:
- a plurality of fiber optic cables, each of said plurality of fiber optic cables mountable near a corresponding exposure area of a corresponding channel.

27. The apparatus of claim 17, wherein said sleeve is formed from a shrink tube material.

28. An electrophoresis apparatus, comprising:
- a gel cartridge assembly, including,
  - a substantially cylindrical column having a longitudinal channel for receiving an electrophoretic gel, said channel being disposed on a peripheral surface of said column, wherein a depth of said channel varies over the length of said channel; and
  - a sleeve configured to cover said peripheral surface of said column and seal said channel at said peripheral surface;
- a container configured to hold said gel cartridge assembly and first and second quantities of a buffer solution, wherein said first quantity of buffer solution and a first end of said gel cartridge assembly are in contact and wherein said second quantity of said buffer solution and a second end of said gel cartridge assembly are in contact to facilitate electrophoresis of a sample contained in said electrophoretic gel;
- a seal configured to mate with the peripheral surface of said gel cartridge assembly and an inner surface of said container to divide said container into a first container portion containing said first quantity of buffer solution and a second container portion containing said second quantity of buffer solution; and
- a base configured to mate with a second end of said gel cartridge assembly to maintain said second end of said gel cartridge assembly in a fixed position within said container.

29. The apparatus of claim 28, comprising:

a plurality of longitudinal channels disposed on said peripheral surface of said column, wherein at least one of said plurality of longitudinal channels has a depth that varies over its length, each said channel being configured to receive said electrophoretic gel.

30. The apparatus of claim 29, wherein a depth of each of said channels is greater than a width of each of said channels.

31. The apparatus of claim 28, wherein said seal is a flexible membrane that seals around said gel cartridge assembly.

32. The apparatus of claim 28, wherein said first container portion further comprises:

a port to allow a flow of said buffer from an external reservoir; and means for relieving an overflow of buffer solution from said first container portion.

33. The apparatus of claim 28, further comprising:

an electrical contact in communication with a voltage source to provide an electrical voltage across said first and second quantities of buffer solution.

34. The apparatus of claim 28, further comprising:

a receptacle located at a selected end of said column to house a light source.

35. The apparatus of claim 28, wherein said sleeve is formed from a shrink tube material.

* * * * *